(12) United States Patent
Choe et al.

(10) Patent No.: US 10,413,724 B2
(45) Date of Patent: Sep. 17, 2019

(54) METHOD FOR LOW LATENCY AUTOMATED CLOSED-LOOP SYNCHRONIZATION OF NEUROSTIMULATION INTERVENTIONS TO NEUROPHYSIOLOGICAL ACTIVITY

(71) Applicant: HRL Laboratories, LLC, Malibu, CA (US)

(72) Inventors: Jaehoon Choe, Agoura Hills, CA (US); Praveen K. Pilly, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/947,733

(22) Filed: Apr. 6, 2018

(65) Prior Publication Data

US 2018/0221661 A1    Aug. 9, 2018

Related U.S. Application Data

(63) Continuation-in-part of application No. 15/332,787, filed on Oct. 24, 2016, now Pat. No. 10,307,592, and
(Continued)

(51) Int. Cl.
*A61N 1/36* (2006.01)
*A61M 21/02* (2006.01)
(Continued)

(52) U.S. Cl.
CPC .......... *A61N 1/36025* (2013.01); *A61B 5/048* (2013.01); *A61B 5/0476* (2013.01);
(Continued)

(58) Field of Classification Search
CPC ............ A61N 1/36025; A61N 1/36031; A61N 1/025; A61N 1/0456; A61M 21/00;
(Continued)

(56) References Cited

U.S. PATENT DOCUMENTS 6,435,876 B1    8/2002  Chen
6,751,505 B1 *  6/2004  Van Den Honert ........................
                                       A61N 1/36036
                                               600/544
(Continued)

FOREIGN PATENT DOCUMENTS

EP          2409641 A1     1/2012
WO     WO 2016-182947 A1  11/2016

OTHER PUBLICATIONS

Notification of Transmittal of International Search Report and the Written Opinion of the International Searching Authority for PCT/US2018/026614; dated Aug. 27, 2018.
(Continued)

*Primary Examiner* — Rex R Holmes
(74) *Attorney, Agent, or Firm* — Tope-McKay & Associates (57) ABSTRACT

Described is a system for synchronization of neurostimulation interventions. The system continuously monitors incoming neurophysiological signals. Latencies present in the monitoring of the incoming neurophysiological signals are measured. Based on the measured latencies, the timing of targeted neurostimulation interventions is determined, resulting in a neurostimulation intervention protocol. The neurostimulation intervention protocol is adjusted in real time for administration of neurostimulation during temporal regions of interest. The system then triggers administration of the neurostimulation during the temporal regions of interest.

15 Claims, 7 Drawing Sheets

Related U.S. Application Data a continuation-in-part of application No. 15/583,983, filed on May 1, 2017.

(60) Provisional application No. 62/245,730, filed on Oct. 23, 2015, provisional application No. 62/330,440, filed on May 2, 2016, provisional application No. 62/516,350, filed on Jun. 7, 2017.

(51) Int. Cl.
| | | |
|---|---|---|
| *A61B 5/0476* | (2006.01) | |
| *A61N 1/02* | (2006.01) | |
| *A61B 5/00* | (2006.01) | |
| *A61B 5/048* | (2006.01) | |
| *A61M 21/00* | (2006.01) | |
| *A61N 1/04* | (2006.01) | |
| *G16H 50/30* | (2018.01) | |

(52) U.S. Cl.
CPC .......... *A61B 5/4806* (2013.01); *A61B 5/4836* (2013.01); *A61B 5/6814* (2013.01); *A61B 5/7264* (2013.01); *A61B 5/7275* (2013.01); *A61B 5/7278* (2013.01); *A61M 21/00* (2013.01); *A61M 21/02* (2013.01); *A61N 1/025* (2013.01); *A61N 1/36031* (2017.08); *A61B 2560/0223* (2013.01); *A61M 2021/0055* (2013.01); *A61M 2021/0072* (2013.01); *A61M 2205/502* (2013.01); *A61M 2205/52* (2013.01); *A61M 2230/10* (2013.01); *A61N 1/0456* (2013.01); *A61N 1/0476* (2013.01); *G16H 50/30* (2018.01)

(58) Field of Classification Search
CPC .......... A61M 21/02; A61M 2021/0055; A61M 2205/502; A61M 2205/52; A61M 2230/10; A61M 2021/0072; A61B 5/048; A61B 5/7264; A61B 5/7278; A61B 5/4806; A61B 5/7275; A61B 5/6814; A61B 5/4836; A61B 5/0476; A61B 2560/0223

See application file for complete search history.

(56) References Cited

U.S. PATENT DOCUMENTS

| | | |
|---|---|---|
| 7,153,139 B2 | 12/2006 | Wen et al. |
| 9,149,599 B2 | 10/2015 | Walter |
| 2003/0225340 A1 | 12/2003 | Collura |
| 2006/0041242 A1 | 2/2006 | Stypulkowski |
| 2007/0060974 A1 | 3/2007 | Lozano |
| 2007/0213786 A1 | 9/2007 | Sackellares et al. |
| 2011/0118534 A1 | 5/2011 | Baror |
| 2011/0159467 A1 | 6/2011 | Peot |
| 2011/0288610 A1 | 11/2011 | Brocke |
| 2012/0184870 A1 | 7/2012 | Shaw |
| 2013/0011817 A1 | 1/2013 | Cohen Kadosh |
| 2013/0225953 A1 | 8/2013 | Oliviero |
| 2013/0288223 A1 | 10/2013 | Watterson |
| 2013/0338738 A1 | 12/2013 | Garcia Molina |
| 2014/0038147 A1 | 2/2014 | Morrow |
| 2014/0288614 A1 | 5/2014 | Hagedorn |
| 2014/0275926 A1 | 9/2014 | Scott et al. |
| 2015/0050623 A1 | 2/2015 | Falash |
| 2015/0066104 A1 | 3/2015 | Wingeier |
| 2015/0079560 A1 | 3/2015 | Cowan |
| 2015/0105837 A1 | 4/2015 | Aguilar Domingo |
| 2015/0174418 A1 | 6/2015 | Tyler |
| 2015/0238762 A1 | 8/2015 | Pal |
| 2015/0294074 A1 | 10/2015 | Kawato |
| 2016/0206871 A1 | 7/2016 | Weisend |
| 2016/0256691 A1 | 9/2016 | Cecchi |
| 2017/0043167 A1 | 2/2017 | Widge |
| 2017/0249853 A1 | 8/2017 | Weiss |
| 2017/0304623 A1 | 10/2017 | Tandon |
| 2018/0169411 A1 | 6/2018 | Goodall |
| 2018/0221644 A1* | 8/2018 | Grill .................. A61N 1/0534 |

OTHER PUBLICATIONS

International Search Report of the International Searching Authority for PCT/US2018/026614; dated Aug. 27, 2018.

Written Opinion of the International Searching Authority for PCT/US2018/026614; dated Aug. 27, 2018.

Bikson, M., Bestmann, S., & Edwards, D. (2013). Neuroscience: transcranial devices are not playthings. Nature, 501(7466), pp. 167-167.

Brunoni, A. R., Nitsche, M. A., Bolognini, N., Bikson, M., Wagner, T., Merabet, L., . . . & Ferrucci, R. (2012). Clinical research with transcranial direct current stimulation (tDCS): challenges and future directions. Brain stimulation, 5(3), pp. 175-195.

Choe, J., Coffman, B. A., Bergstedt, D. T., Ziegler, M. D., & Phillips, M. E. (2016). Transcranial direct current stimulation modulates neuronal activity and learning in pilot training. Frontiers in human neuroscience, 10, pp. 1-25.

Schultz DM, Webster L, Kosek P, et al. Sensor-driven position-adaptive spinal cord stimulation for chronic pain. Pain Physician 2012;15: pp. 1-12.

Jacobson, L., Koslowsky, M., & Lavidor, M. (2012). tDCS polarity effects in motor and cognitive domains: a meta-analytical review. Experimental brain research, 216(1), pp. 1-10.

Osorio I, Frei MG, Sunderam S, et al. Automated seizure abatement in humans using electrical stimulation. Ann Neurol 2005;57: pp. 258-268.

Berényi, A., Belluscio, M., Mao, D., & Buzsáki, G. (2012). Closed-loop control of epilepsy by transcranial electrical stimulation. Science, 337(6095), pp. 735-737.

Tergau, F., Naumann, U., Paulus, W., & Steinhoff, B. J. (1999). Low-frequency repetitive transcranial magnetic stimulation improves intractable epilepsy. The Lancet, 353(9171), p. 2209.

Nitsche, M. A., Cohen, L. G., Wassermann, E. M., Priori, A., Lang, N., Antal, A., . . . & Pascual-Leone, A. (2008). Transcranial direct current stimulation: state of the art 2008. Brain stimulation, 1(3), pp. 206-223.

Ferrucci, R., Mameli, F., Guidi, I., Mrakic-Sposta, S., Vergari, M., Marceglia, S. E. E. A., . . . & Priori, A. (2008). Transcranial direct current stimulation improves recognition memory in Alzheimer disease. Neurology, 71(7), pp. 493-498.

Clark, V. P., Coffman, B. A., Mayer, A. R., Weisend, M. P., Lane, T. D., Calhoun, V. D., . . . & Wassermann, E. M. (2012). TDCS guided using fMRI significantly accelerates learning to identify concealed objects. Neuroimage, 59(1), pp. 117-128.

Gálvez-García, G., Albayay, J., Rehbein, L., & Tomay, F. (2017). Mitigating Simulator Adaptation Syndrome by means of tactile stimulation. Applied Ergonomics, 58, pp. 13-17.

Ngo, H. V. V., Miedema, A., Faude, I., Martinetz, T., Molle, M., & Born, J. (2015). Driving Sleep Slow Oscillations by Auditory Closed-Loop Stimulation—A Self-Limiting Process. The Journal of Neuroscience, 35(17), pp. 6630-6638.

Cox, R., Korjoukov, I., de Boer, M., & Talamini, L. M. (2014). Sound asleep: processing and retention of slow oscillation phase-targeted stimuli. PloS one, 9(7), e101567, pp. 1-12.

Santostasi, G., Malkani, R., Riedner, B., Bellesi, M., Tononi, G., Paller, K. A., & Zee, P. C. (2016). Phase-locked loop for precisely timed acoustic stimulation during sleep. Journal of neuroscience methods, 259, pp. 101-114.

van Elmpt WJ, Nijsen TM, Griep PA, et al. A model of heart rate changes to detect seizures in severe epilepsy. Seizure 2006;15: pp. 366-375.

Schade CM, Schultz DM, Tamayo N, et al. Automatic adaptation of neurostimulation therapy in response to changes in patient position: results of the Posture Responsive Spinal Cord Stimulation (PRS) Research Study. Pain Physician 2011;14: pp. 407-417.

(56) References Cited

OTHER PUBLICATIONS

Little S, Pogosyan A, Neal S, et al. Adaptive deep brain stimulation in advanced Parkinson disease. Ann Neurol 2013;74: pp. 449-457.
Notice of Allowance for U.S. Appl. No. 15/332,787, dated Jan. 17, 2019.
Merzagora, Anna C., G. Foffani, I. Panyavin, L. Mordillo-Mateos, J. Aguilar, Banu Onaral, and A. Oliviero. "Prefrontal hemodynamic changes produced by anodal direct current stimulation." Neuroimage 49, No. 3 (2010): pp. 2304-2310.
Christoff, J. A. (2002). Foreign Languages: Human Capital Approach Needed to Correct Staffing and Proficiency Shortfalls. Report to Congressional Requesters, pp. 1-50.
Operation and Maintenance Overview, Fiscal Year 2016 Budget Estimates, Feb. 2015, Office of the Under Secretary of Defense (Comptroller) / Chief Financial Officer, p. 13.
Flöel, A., Rösser, N., Michka, O., Knecht, S., & Breitenstein, C. (2008). Noninvasive brain stimulation improves language learning. Journal of Cognitive Neuroscience, 20(8), pp. 1415-1422.
Fregni, F., Boggio, P. S., Nitsche, M., Bermpohl, F., Antal, A., Feredoes, E., . . . & Pascual-Leone, A. (2005). Anodal transcranial direct current stimulation of prefrontal cortex enhances working memory. Experimental brain research, 166(1), pp. 23-30.
Acheson, D. J., Hamidi, M., Binder, J. R., & Postle, B. R. (2011). A common neural substrate for language production and verbal working memory. Journal of Cognitive Neuroscience, 23(6), pp. 1358-1367.
Anderson, J. R. (1981). Cognitive skills and their acquisition. Psychology Press. pp. 143-146 and pp. 243-249.
Bates, E., & MacWhinney, B. (1989). Functionalism and the competition model. The crosslinguistic study of sentence processing, 3, pp. 73-112.
Pienemann, M. (2005). An introduction to processability theory. Cross-linguistic aspects of processability theory, 30, pp. 179-199.
Schumann, J. H. (1986). Research on the acculturation model for second language acquisition. Journal of multilingual & multicultural development, 7(5), pp. 379-392.
Marshall L, Helgadóttir H, Mölle M, Born J. Boosting slow oscillations during sleep potentiates memory. Nature. 2006; 444(7119): pp. 610-613.
Rudoy JD, Voss JL, Westerberg CE, Paller KA. Strengthening Individual Memories by Reactivating Them During Sleep. Science. Nov. 20, 2009;326(5956): pp. 1079-1079.
Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.
Rasch BH, Born J, Gais S. Combined blockade of cholinergic receptors shifts the brain from stimulus encoding to memory consolidation. J Cogn Neurosci. May 2006; 18(5): pp. 793-802.
Gais S, Born J. Low acetylcholine during slow-wave sleep is critical for declarative memory consolidation. Proc Natl Acad Sci U S A. Feb. 17, 2004; 101(7): pp. 2140-2144.
Rasch B, Buchel C, Gais S, Born J. Odor cues during slow-wave sleep prompt declarative memory consolidation. Science. 2007; 315(5817): pp. 1426-1429.
Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.
Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.
Brincat SL, Miller EK. Frequency-specific hippocampal-prefrontal interactions during associative learning. Nat Neurosci. Apr. 2015; 18(4): pp. 576-581.
McNamara CG, Tejero-Cantero A, Trouche S, Campo-Urriza N, Dupret D. Dopaminergic neurons promote hippocampal reactivation and spatial memory persistence. Nat Neurosci. 2014 12//print; 17(12): pp. 1658-1660.
Ji D, Wilson MA. Coordinated memory replay in the visual cortex and hippocampus during sleep. Nat Neurosci. 2007; 10(1): pp. 100-107.
Kali S, Dayan P. Off-line replay maintains declarative memories in a model of hippocampal-neocortical interactions. Nat Neurosci. 2004; 7(3): pp. 286-294.
Rolls ET. Hippocampo-cortical and cortico-cortical backprojections. Hippocampus. 2000; 10: pp. 380-388.
Creutzfeldt OD, Fromm GH, Kapp H. Influence of transcortical d-c currents on cortical neuronal activity. Exp Neurol. Jun. 1962; 5: pp. 436-452.
Sederberg PB, Kahana MJ, Howard MW, Donner EJ, Madsen JR. Theta and gamma oscillations during encoding predict subsequent recall. J Neurosci Off J Soc Neurosci. Nov. 26, 2003; 23(34): pp. 10809-10814.
Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.
Fröhlich F, McCormick DA. Endogenous electric fields may guide neocortical network activity. Neuron. Jul. 15, 2010; 67(1): pp. 129-143.
Ngo, H. V. V., Martinetz, T., Born, J., & Mölle, M. (2013). Auditory closed-loop stimulation of the sleep slow oscillation enhances memory. Neuron, 78(3), pp. 545-553.
Office Action 1 for U.S. Appl. No. 15/583,983, dated Feb. 12, 2019.
Apoorvagiri; Mental Stress and its Implications on Reaction time; International Journal of Computer Trends and Technology; May 2013; Mental Stress and its Imprilcations on Reaction time. (Year 2013).
Office Action 1 for U.S. Appl. No. 15/332,787, dated Sep. 18, 2018.
Response to Office Action 1 for U.S. Appl. No. 15/332,787, dated Nov. 6, 2018.

\* cited by examiner

METHOD FOR LOW LATENCY AUTOMATED CLOSED-LOOP SYNCHRONIZATION OF NEUROSTIMULATION INTERVENTIONS TO NEUROPHYSIOLOGICAL ACTIVITY

CROSS-REFERENCE TO RELATED APPLICATIONS

This is a Continuation-in-Part patent application of U.S. application Ser. No. 15/332,787, filed in the United States on Oct. 24, 2016, entitled, "Method and System to Accelerate Consolidation of Specific Memories Using Transcranial Stimulation," which is a Non-Provisional patent application of U.S. Provisional Application No. 62/245,730, filed in the United States on Oct. 23, 2015, entitled, "Method and System to Accelerate Consolidation of Specific Memories Using Transcranial Stimulation," the entirety of which are hereby incorporated by reference.

This is ALSO a Continuation-in-Part patent application of U.S. application Ser. No. 15/583,983, filed in the United States on May 1, 2017, entitled, "System and Method for Neurostimulation-Enhanced Second Language Acquisition," which is a Non-Provisional patent application of U.S. Provisional Application No. 62/330,440, filed in the United States on May 2, 2016, entitled, "A Method for Neurostimulation-Enhanced Second Language Acquisition," the entirety of which are hereby incorporated by reference.

This is ALSO Non-Provisional patent application of U.S. Provisional Application No. 62/516,350, filed in the United States on Jun. 7, 2017, entitled, "A Method for Low Latency Automated Closed-Loop Synchronization of Neurostimulation Interventions to Neurophysiological Activity," the entirety of which is hereby incorporated by reference.

STATEMENT REGARDING FEDERALLY SPONSORED RESEARCH OR DEVELOPMENT

This invention was made with government support under U.S. Government Contract Number W911NF-16-C-0018. The government may have certain rights in the invention.

BACKGROUND OF INVENTION

(1) Field of Invention

The present invention relates to a system for automatically applying low-latency brain stimulation and, more particularly, to a system for automatically applying low-latency brain stimulation using neurophysiological signals to trigger and adapt delivered currents.

(2) Description of Related Art

Neuromodulation is a therapy that can involve a range of electromagnetic stimuli such as a strong magnetic field, a very small electric current, or a drug instilled directly in the subdural space. Previous work in research papers by Ngo et al. (see the List of Incorporated Literature References, Literature Reference No. 13), Cox et al. (see Literature Reference No. 14), and Santostasi et al. (see Literature Reference No. 15) have proposed methods to automatically trigger neuromodulatory stimulation in response to ongoing neurophysiological activity for augmenting brain states of interest during sleep. Ngo et al. (see Literature Reference No. 13) does not attempt to identify/classify a continuously recorded signal, but instead uses a simple threshold crossing to trigger intervention.

Cox et al. (see Literature Reference No. 14) suggests metrics to detect brain states of interest, but only uses that information to initiate state-based triggering of static audio stimuli. The stimulation is triggered by, but not adapted to, information derived from detected brain states. Santostasi et al. demonstrates a system that utilizes a phase-locked loop that detects brain states, uses this information to trigger the intervention, and adapts stimuli in limited fashion based on the brain state information. However, the adaptation is not individualized to subjects, using the same threshold criteria for stimulation for all users, ignoring variations in individual neurophysiological properties. While this method uses a continuous method of generating stimulation predictions, the technique only predicts phase and frequency of the projected signal. Finally, similar to Cox et al., Santostasi et al. applies only an audio-based stimulation that is several levels removed from actual neural activity.

In other domains, closed-loop stimulation alleviating symptoms of chronic pain have been commercialized using body position as the physiological trigger for intervention (see Literature Reference No. 17). This method uses only body kinematics as an abstracted version of neurophysiology for state-based triggering and utilizes only a predetermined library of stimulation protocols that is not processed or adapted based on the recorded information or tailored to the individual. For epilepsy, Osorio et al. have developed a system using recorded brain signals to initiate electrical stimulation intended to stop seizure activity (see Literature Reference No. 6). The recorded signals and the algorithm to stimulate is explicitly stated to be non-predictive, and stimulation still occurs as delivery of a predetermined, static protocol. More recent implementations of cardiac rhythm as a predictor of seizures (see Literature Reference No. 16) likewise do not address the adaptation and personalization aspects of intervention systems.

The state-of-the-art currently focuses on the triggering of intervention or predictive detection of brain states in isolation. Thus, a continuing need exists for a neuromodulation system for generating adaptive, automatic neurostimulation interventions from real-time monitoring of biological signals.

SUMMARY OF INVENTION

The present invention relates to a system for automatically applying low-latency brain stimulation and, more particularly, to a system for automatically applying low-latency brain stimulation using neurophysiological signals to trigger and adapt delivered currents. The system comprises one or more processors and a non-transitory computer-readable medium having executable instructions encoded thereon such that when executed, the one or more processors perform multiple operations. The system continuously monitors incoming neurophysiological signals and measures latencies present in the monitoring of the incoming neurophysiological signals. Based on the measured latencies, the system determines timing of targeted neurostimulation interventions, resulting in a neurostimulation intervention protocol. The neurostimulation intervention protocol is adjusted in real time for administration of neurostimulation during temporal regions of interest. Finally, the system administers neurostimulation during the temporal regions of interest.

In another aspect, the system classifies the incoming neurophysiological signals and adapts the administered neurostimulation according to the classified incoming neurophysiological signals.

In another aspect, properties of the incoming brain signals are replicated at the time of neurostimulation.

In another aspect, the system verifies that the administered neurostimulation replicates the properties of the incoming brain signals.

In another aspect, the triggering of the administration of the neurostimulation is calibrated to a set of predetermined neurophysiological signals.

In another aspect, the system determines potential time points of neurostimulation during which the administered neurostimulation matches predicted neurophysiological signals for slow-wave sleep augmentation.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a system for automatically applying low-latency brain stimulation and, more particularly, to a system for automatically applying low-latency brain stimulation using neurophysiological signals to trigger and adapt delivered currents. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) LIST OF INCORPORATED LITERATURE REFERENCES

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Bikson, M., Bestmann, S., & Edwards, D. (2013). Neuroscience: transcranial devices are not playthings. Nature, 501(7466), 167-167.
2. Brunoni, A. R., Nitsche, M. A., Bolognini, N., Bikson, M., Wagner, T., Merabet, L., . . . & Ferrucci, R. (2012). Clinical research with transcranial direct current stimulation (tDCS): challenges and future directions. Brain stimulation, 5(3), 175-195.
3. Choe, J., Coffman, B. A., Bergstedt, D. T., Ziegler, M. D., & Phillips, M. E. (2016). Transcranial direct current stimulation modulates neuronal activity and learning in pilot training. Frontiers in human neuroscience, 10.
4. Schultz D M, Webster L, Kosek P, et al Sensor-driven position-adaptive spinal cord stimulation for chronic pain. Pain Physician 2012; 15:1-12.
5. Jacobson, L., Koslowsky, M., & Lavidor, M. (2012). tDCS polarity effects in motor and cognitive domains: a meta-analytical review. Experimental brain research, 216 (1), 1-10.

6. Osorio I, Frei M G, Sunderam S, et al. Automated seizure abatement in humans using electrical stimulation. Ann Neurol 2005; 57:258-268.
7. Berényi, A., Belluscio, M., Mao, D., & Buzsáki, G. (2012). Closed-loop control of epilepsy by transcranial electrical stimulation. Science, 337(6095), 735-737.
8. Tergau, F., Naumann, U., Paulus, W., & Steinhoff, B. J. (1999). Low-frequency repetitive transcranial magnetic stimulation improves intractable epilepsy. The Lancet, 353(9171), 2209.
9. Nitsche, M. A., Cohen, L. G., Wassermann, E. M., Priori, A., Lang, N., Antal, A., . . . & Pascual-Leone, A. (2008). Transcranial direct current stimulation: state of the art 2008. Brain stimulation, 1(3), 206-223.
10. Ferrucci, R., Mameli, F., Guidi, I., Mrakic-Sposta, S., Vergari, M., Marceglia, S. E. E. A., . . . & Priori, A. (2008). Transcranial direct current stimulation improves recognition memory in Alzheimer disease. Neurology, 71(7), 493-498.
11. Clark, V. P., Coffman, B. A., Mayer, A. R., Weisend, M. P., Lane, T. D., Calhoun, V. D., . . . & Wassermann, E. M. (2012). TDCS guided using fMRI significantly accelerates learning to identify concealed objects. Neuroimage, 59(1), 117-128.
12. Gálvez-García, G., Albayay, J., Rehbein, L., & Tornay, F. (2017). Mitigating Simulator Adaptation Syndrome by means of tactile stimulation. Applied Ergonomics, 58, 13-17.
13. Ngo, H. V. V., Miedema, A., Faude, I., Martinetz, T., Mölle, M., & Born, J. (2015). Driving Sleep Slow Oscillations by Auditory Closed-Loop Stimulation—A Self-Limiting Process. The Journal of Neuroscience, 35(17), 6630-6638.
14. Cox, R., Korjoukov, I., de Boer, M., & Talamini, L. M. (2014). Sound asleep: processing and retention of slow oscillation phase-targeted stimuli. PloS one, 9(7), e101567.
15. Santostasi, G., Malkani, R., Riedner, B., Bellesi, M., Tononi, G., Paller, K. A., & Zee, P. C. (2016). Phase-locked loop for precisely timed acoustic stimulation during sleep. Journal of neuroscience methods, 259, 101-114.
16. van Elmpt W J, Nijsen T M, Griep P A, et al. A model of heart rate changes to detect seizures in severe epilepsy. Seizure 2006; 15:366-375.
17. Schade C M, Schultz D M, Tamayo N, et al. Automatic adaptation of neurostimulation therapy in response to changes in patient position: results of the Posture Responsive Spinal Cord Stimulation (PRS) Research Study. Pain Physician 2011; 14: 407-417.
18. Little S, Pogosyan A, Neal S, et al. Adaptive deep brain stimulation in advanced Parkinson disease. Ann Neurol 2013; 74:449-457.

(2) PRINCIPAL ASPECTS

Various embodiments of the invention include three "principal" aspects. The first is a system for automatically applying low-latency brain stimulation. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
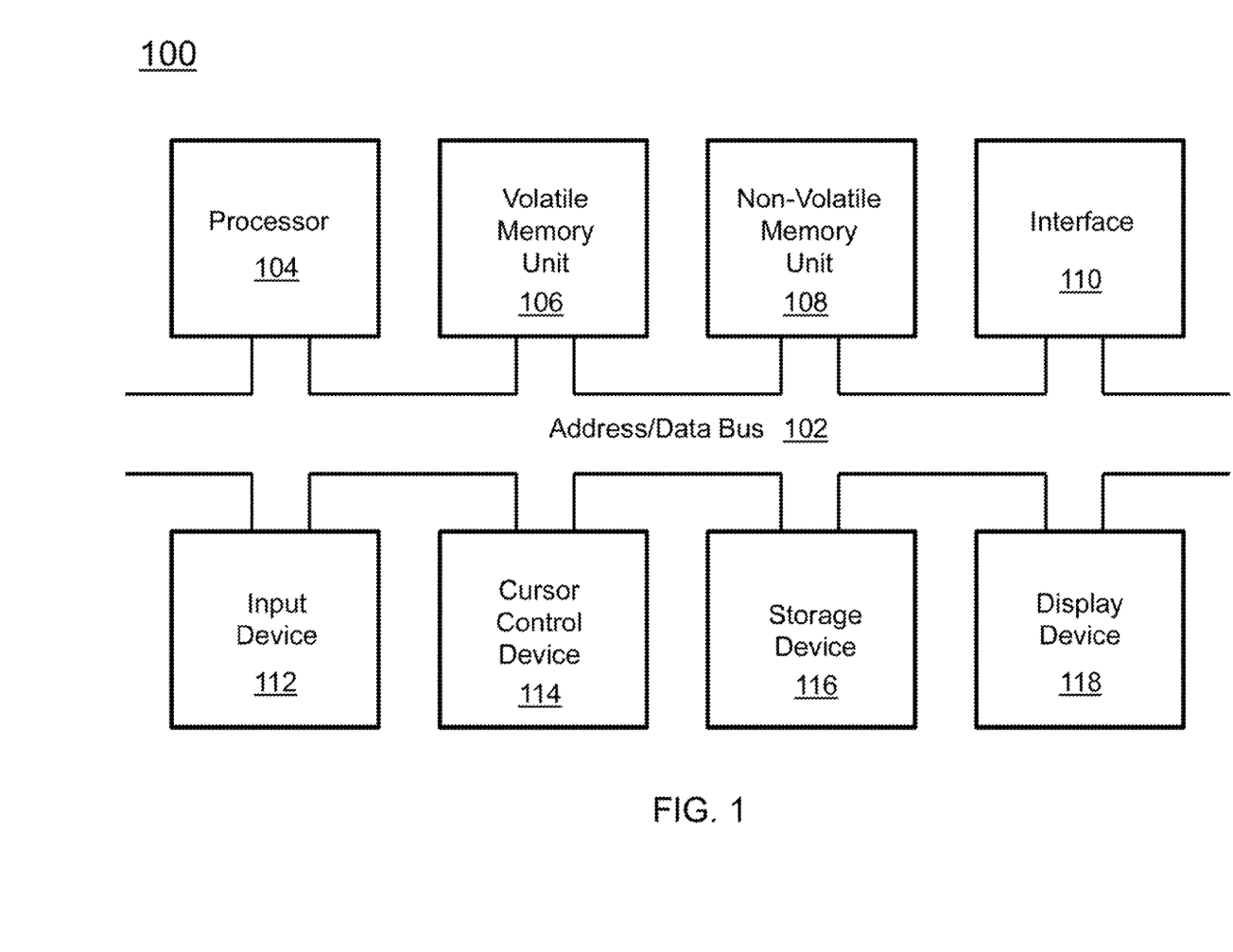
FIG. 1 is a block diagram depicting the components of a system for automatically applying low-latency brain stimulation according to some embodiments of the present disclosure.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
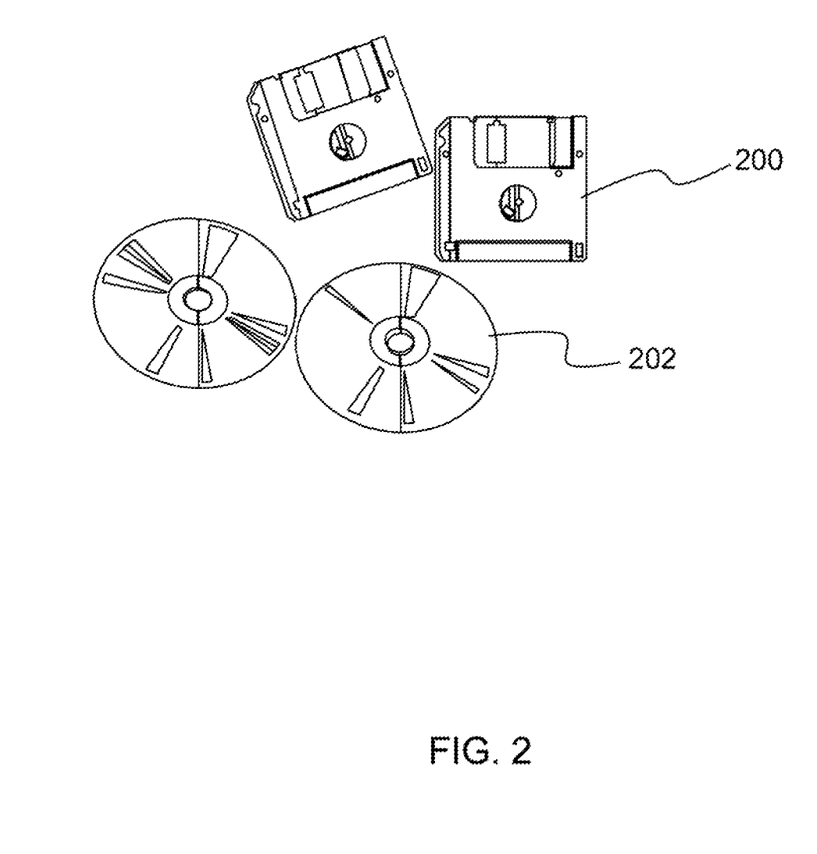
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) SPECIFIC DETAILS OF VARIOUS EMBODIMENTS

Described is a system and method for automatically applying low-latency brain stimulation (invasive and non-invasive), including transcranial alternating current (tACS) interventions, in closed loop, using neurophysiological signals to trigger and adapt delivered currents. Examples of non-invasive stimulation include transcranial current stimulation (tCS) and transcranial magnetic stimulation (TMS). The invention described herein allows a human participant outfitted with neural recording devices to receive a personalized, targeted brain stimulation intervention in response to the detection of specific neurophysiological cues, a capability essential for the development of a variety of emergent neurostimulation technologies.

A unique aspect of this invention is the autonomy of operation. Once initially set up, the software and hardware elements are designed to interact without human supervision to apply neurostimulation interventions derived from real-time monitoring of biological signals. This capability, enabled by automated classification of incoming neural signals and adaptation to individual physiology, tightly integrates the detection and stimulation infrastructure in software and hardware. Adaptive, automatic stimulation interventions are critical for a path to the commercialization of a diverse array of neuromodulation and neurostimulation technologies.

Figure 3:
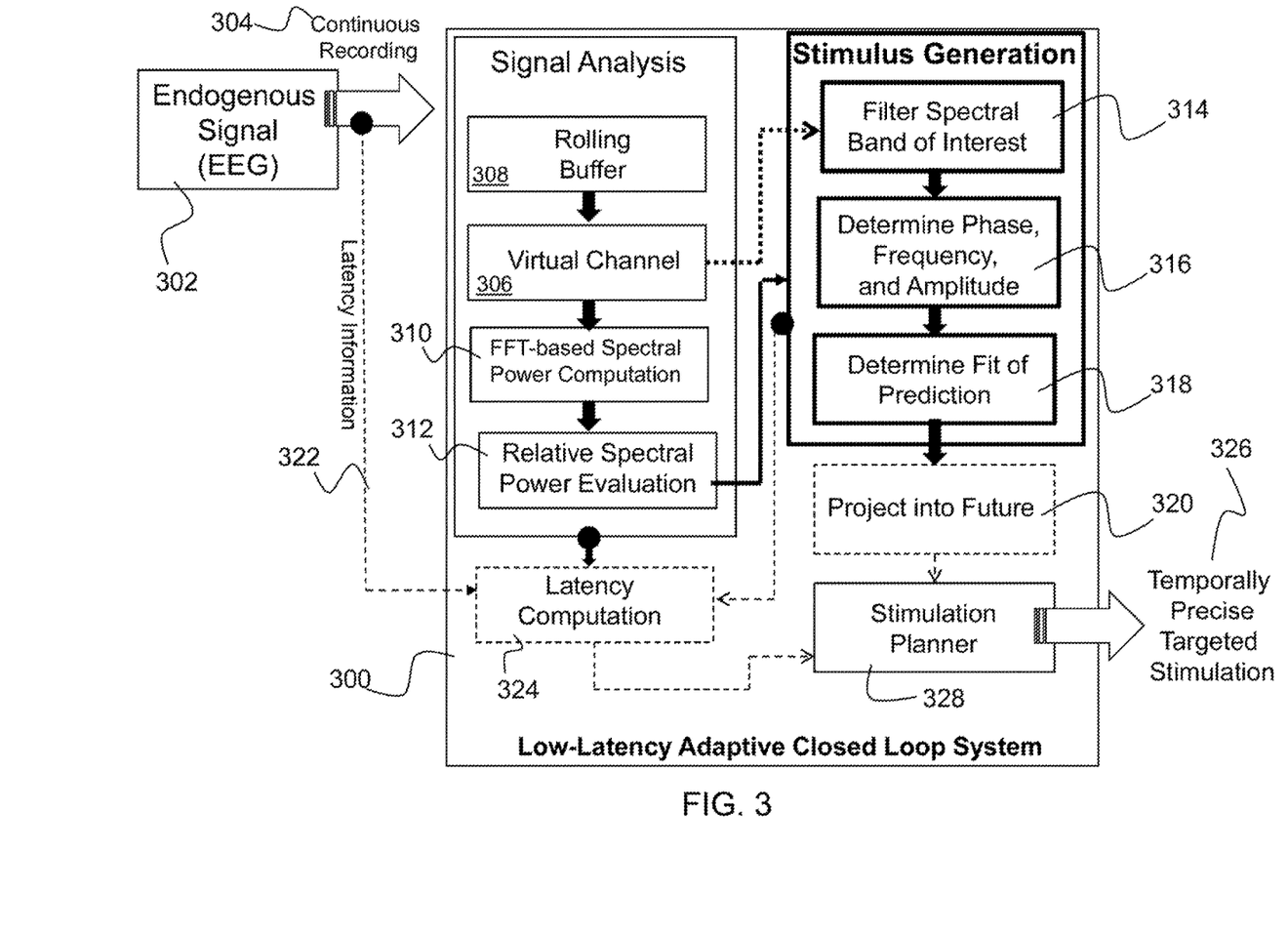
FIG. 3 is a flow diagram illustrating a low-latency adaptive closed-loop system according to some embodiments of the present disclosure.

Continuous monitoring of biological signals is necessary as each step within the closed-loop process requires consideration for latencies throughout the system, whether they be caused by computation time, transmission delays, or other sources of temporal delay that affect the timing of a stimulation intervention. The system is designed to measure real latencies that arise through normal operation, and uses this information for more accurate targeting of stimulation. This is connected intimately with the stimulation generation system (elements 314-318), in which the signal encoded into the intervention (e.g., a SWO-frequency-matched sine wave) is completely dependent on the properties of the coincident physiological signal. As illustrated in FIG. 3, the latency computer (element 324) is a critical part of the closed-loop intervention, informing the stimulation generation steps as well as defining the precise time point in which the stimulation must be administered (elements 314-328). The result is a continuously adaptive, highly accurate closed-loop stimulation system that accounts for real-world computing and transmission delays in real time, delivering highly accurate, physiologically-triggered stimulation interventions. The neurostimulation intervention protocol is adjusted in real time by this system for administration of neurostimulation at temporally precise regions of interest. After this closed-loop operation has been completed, the system administers neurostimulation at an optimally scheduled time interval and heuristically determines whether the hardware is physically capable of meeting critical stimulation time envelopes (e.g., processing and transmission times must allow for stimulation in a specific window roughly one slow-wave oscillation period long). Should the system-level delays go beyond the stimulation requirement, the closed-loop components will not trigger an intervention, rather returning to physiological signal detection mode to wait for the next intervention opportunity.

Closed-loop neuromodulation relies upon many software and hardware elements working in close synchrony to deliver and adapt targeted stimulation triggered from neurophysiological events processed in real time. As a result, a suite of neurophysiological signal analysis and brain stimulation software was developed, as described herein, that internally identifies the timing of tasks that precisely aligns interventions to observations (e.g., ongoing slow-wave activity in sleep), predicted events (e.g., upcoming positive half-wave of ongoing slow-wave oscillations (SWO) in sleep), or brain states (e.g., memory encoding states indexed by brain-wide spectral power signatures) despite the constraints imposed by latencies arising from computing and communications.

The stimulation intervention (stimulation protocol) is derived from recorded endogenous signals and computed in real time to maximize neuromodulatory effects. This is achieved through replication of the amplitude, frequency, and other properties of the user's ongoing physiology at the time of stimulation (such as, slow wave oscillations). The accuracy of the system according to embodiments of this disclosure is achieved due to the signal of ongoing endogenous signals being verified in a series of checks to ensure the applied stimulation replicates the properties of the ongoing brain signals. Further, the triggering of the intervention is calibrated to the neurophysiological signatures of each individual user, further ensuring the fidelity of the stimulation protocol to personalized physiology.

Thus, the system according to embodiments of the present disclosure enables the following critical aspects of effective closed-loop neurostimulation intervention: 1) Precise timing of interventions to ensure that modulation of neural activity occurs during the temporal regions of interest, enabling selective targeting of specific, potentially transient phenomena; and 2) Adaptation and replication of brain signals specific to the user of the device, maximizing the probability of effecting changes to the user over continuous timescales. The combination of these capabilities allows for the construction of devices that can operate without the need for expert operators or controlled laboratory environments that administer personalized interventions to users of neurotherapeutic or neuroaugmentative devices.

FIG. 3 depicts the architecture of a low-latency adaptive closed-loop system 300 according to embodiments of the present disclosure. An electroencephalogram (EEG) recording device 302 (or any other suitable neural recording device) collects continuous, endogenous neurophysiological signals 304 for the purposes of classification and brain state detection. Note the neurophysiological signals can also be sensed by other means, such as implanted multi-electrode arrays (e.g., Utah) and electrocorticography (ECoG). A Virtual Channel 306 is generated, providing an EEG signal that describes large-scale, synchronized changes of EEG potentials that are continually stored in a rolling buffer 308 of variable length. The algorithm described herein then applies a Fast-Fourier Transform (FFT-based Spectral Computation 310) to the stored data to determine the strength of the neurophysiological activity across different frequency bands. If the signal meets spectrum-based power criteria (relative power in a selected band) (i.e., relative spectral power evaluation 312), the algorithm then filters the endogenous data to generate a smoother band-specific form of the endogenous signals (i.e., filter spectral band of interest 314).

Simultaneously, for slow-wave oscillation (SWO) augmentation during sleep, the algorithm generates a sine wave based on the identified dominant frequency in the band of interest and optimizes for amplitude, offset, and phase properties of the endogenous signal as a seed for the predictive output (i.e., determine phase, frequency, and amplitude 316). The sine wave is then compared to the filtered endogenous data, and the closeness of fit is determined using a mean squared error (MSE) metric (i.e., determine fit of prediction 318). Should this generated sine wave meet the fit criteria (i.e., MSE below a specified threshold), the signal is then projected into the future (element 320), identifying targets of stimulation that would synchronize brain stimulation to the predicted endogenous signal (e.g., tACS to the predicted UP states during slow-wave sleep).

Throughout this process, the latencies associated with data collection, computation, and transmission (i.e., latency information 322) are all assessed (i.e., latency computation 324) to achieve temporally precise targeted stimulation 326. This determines potential time points of stimulation, during which the applied tACS would match the predicted neural activity of the user for slow-wave sleep augmentation. Should processing times push beyond any potential stimulation time point, the algorithm compares the current time to the (now deprecated) stimulation time, and plans the stimulation (i.e., stimulation planner 328) for the next available stimulation time point. Once stimulation is delivered, the predictive system is placed idle to avoid the collection of stimulation artifacts, then resumes, re-entering the cycle of signal recording in preparation for the next stimulation event. A key aspect of this architecture is the continuous collection of data (element 304). Endogenous neurophysiological activity is constantly added to a buffer of stored data (i.e., rolling buffer 308) to generate the predictive projection. In this way, the system is able to adapt constantly to ongoing events in the user's physiology in order to generate the most accurate prediction of future SWO activity available.

(3.1) Issues of Data Latency

Figure 4:
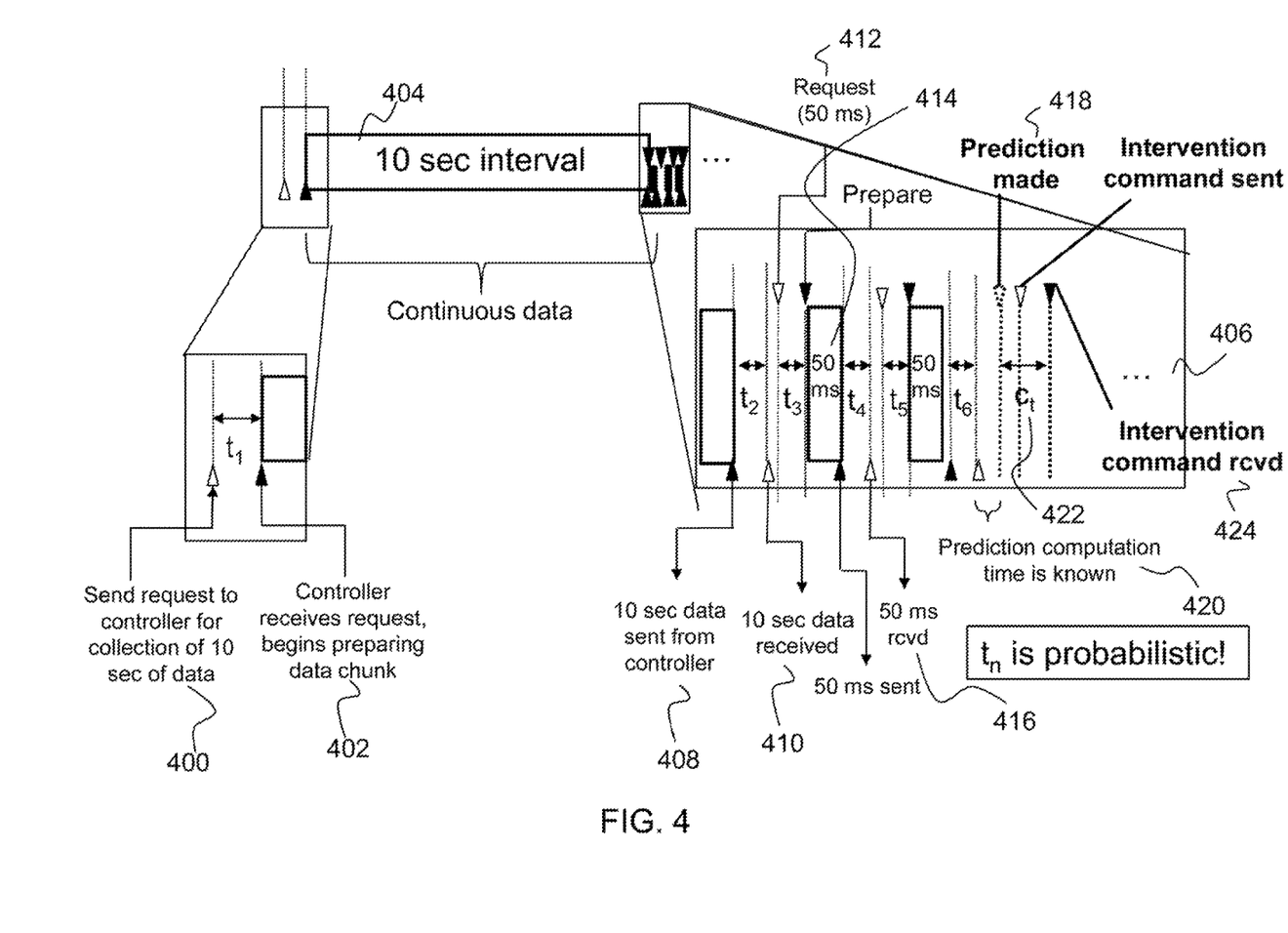
FIG. 4 is an illustration of sources of latencies in a real-world digital sampling scenario according to some embodiments of the present disclosure.

In any recording/stimulation setup, latencies exist during data collection, computation, and transmission phases that are non-trivial in the timescale of tACS or other brain stimulation interventions. FIG. 4 depicts sources of latencies in a real-world digital sampling scenario, assuming 10-second buffer storage. The system begins by using the resident algorithm of the computer to send a request to the controller device to buffer 10 seconds of data in computer memory at a given time (element 400). A non-limiting example of a controller device is a mobile phone, loaded with an app with the algorithm's functionality included within the software package. Similarly, a non-limiting example of the controller device is a wireless, bidirectional (recording/stimulation) multichannel hub that is connected to recording hardware, such as a head cap with embedded non-invasive electrodes. Data from these sensors would be requested by the computer, and the controller would deliver said information into the computer memory. Additionally, stimulation commands from the computer are transmitted to the controller, which will then perform intervention function at specified time points in the future.

Note that in FIG. 4, filled arrows indicate incoming/outgoing transmissions from the controller, whereas open arrows indicate incoming/outgoing transmissions for the computer. The computer performs the action described in element 400, and the device performs the actions described in element 402. Because of inherent delays in transmitting data and receiving it over the hardware interfaces that comprise the interconnection between the computer and controller device, the algorithm computes transmission delay time from the controller device to the sensor controller $t_1$ based on the internal clocks of the controller (element 402). The controller device is also responsible for compensating for the measured transmission delays in addition to continually running the algorithm as a component of the overall closed-loop system.

Figure 5:
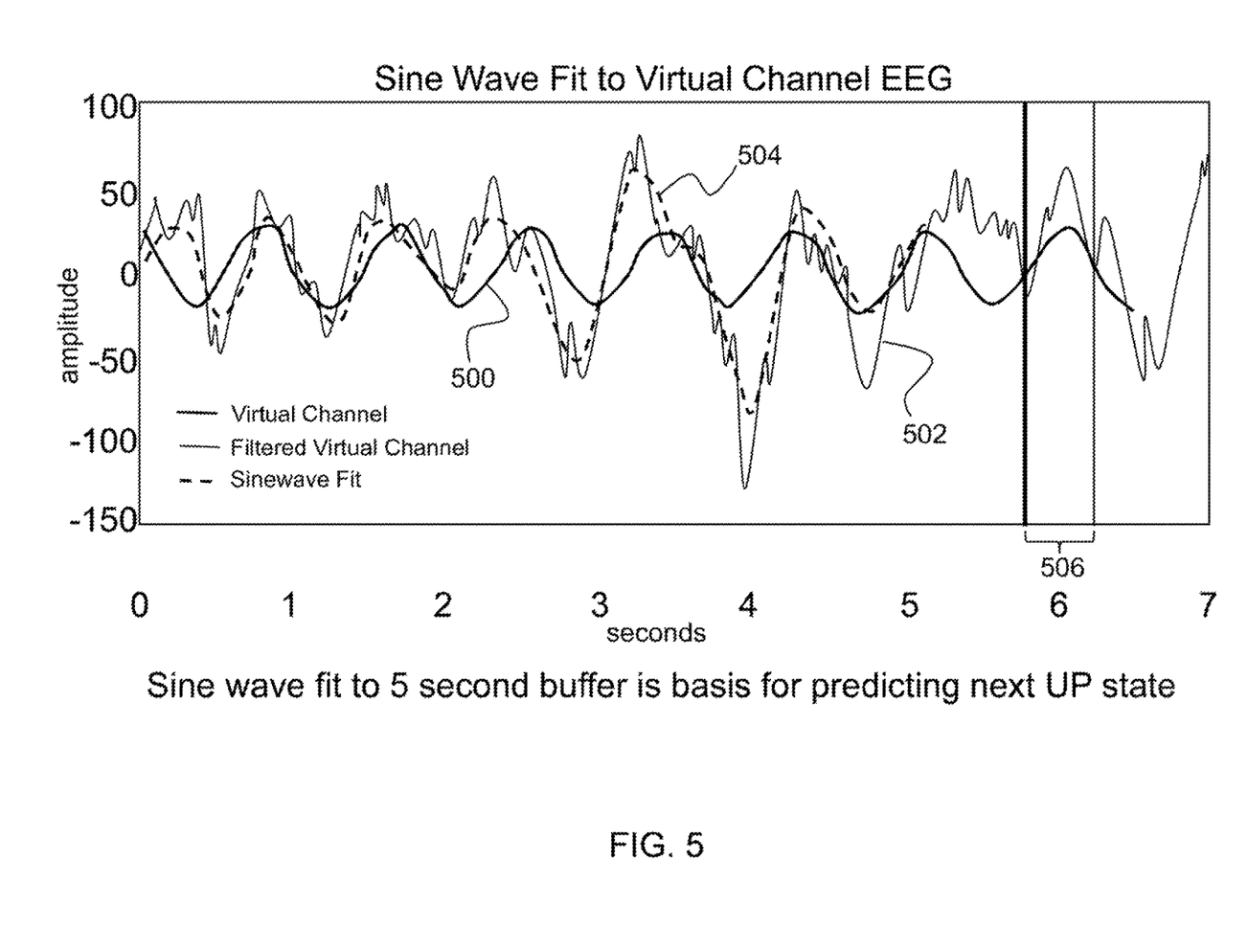
FIG. 5 is an illustration of filtering raw virtual signal through slow-wave oscillation (SWO) bandpass window.

The combined hardware/software device executes elements 400 and 402, and the result of executing elements 400 and 402 leads to the storage of 10 seconds of biological neural data (element 404) into computer memory. The time duration of element 404 is always maintained at 10 seconds (or other predetermined time), with an additional, short-duration time series signal being appended constantly and an equivalent duration of signal being discarded from the beginning of the buffer to keep element 404 up-to-date. Element 404 is the data from which the properties of the stimulation are computed as depicted in FIGS. 3 and 5.

Element 406 describes the functions of the computer/controller system subsequent to the initial data request, in which the buffer information in computer memory must be continually updated. Furthermore, should conditions for intervention be met (i.e., detection of specific neurophysiological cues), stimuli must be timed and scheduled precisely to events occurring in the brain, accounting for delays arising from interconnections within the system and the time requirements for signal processing. Here, the transmission delay for data request is $t_1$ for the beginning of the process defined by elements 400 and 402. The transmission delay associated with post-recording (i.e., the time it takes for element 404 to reach the computer memory) is represented as $t_2$. In element 406, similar transmission delay factors (albeit for much shorter-duration signal requests) are represented by $t_n$. For clarity, element 410 is the precise time point when the initial 10 seconds buffer data is fully requested by the computer, transmitted over inter-device communications (computer to controller), prepared by the controller, then transmitted again through inter-device communications (controller to computer). Element 412 is a repeat of the process begun at element 400, but the duration of buffer is reduced to 50 milliseconds to update the stored buffer (element 404).

The computer manipulates element 404 in memory such that the new data segment (element 414) is appended to element 404, and an equivalent length of data is truncated from the start of element 404. The effect is that the buffer is maintained at 10 seconds (or other time as appropriate), but element 404 is continually updated such that it represents the neural data from 10 seconds in the past precisely from when the request was sent at element 412. Elements 408 and 410 described above are analogous to elements 412 and 416, and the data requested (element 404) is analogous to the update data requested (element 414). This process (elements 410-416) is repeated and the operations described in FIGS. 3 and 5 are performed on the signal by the computer, until conditions are met for stimulation (i.e., detection of specific neurophysiological cues). Once this is achieved, the next point of intervention (coinciding with a predicted slow wave peak) is scheduled for intervention (element 418), which occurs over some measurable processing time (element 420). This time must be accounted for in addition to an estimate for the transmission time for sending the intervention command $c_t$ (element 422) to place the intervention in the correct temporal location.

Note that the intervention command is received by the controller at element 424, but the system may have chosen some time in the future or past for the intervention which should be evident once the next time slice (additional instances of element 414) are collected by the controller. As a result, the computer determines whether intervention falls within some time window in the future and if this target has been exceeded, generates a new intervention schedule that targets the next available slow wave peak and undergoes the process described through elements 418-424 again. If the time since the detection of the slow wave oscillations (SWO) exceeds physiological values for SWO activity duration (~3-5 seconds), the intervention may be cancelled altogether and the computer and controller unit resumes the normal operation beginning again at element 400.

A closed-loop system must account for and adjust stimulation parameters in real time in order to ensure the proper administration of stimulation at the correct temporal targets. To achieve this, every aspect of the data collection-computation-signal transmission pipeline must be timed, and the distributions for various latencies are constantly updated. The algorithm described herein places timers on all aspects of data collection (transmission delay), data analysis (compute time), and data transmission (transmission of command signals), constantly updating the delay involved for stimulation intervention, as shown in FIG. 4. The start and end of each of the various operations are read out from the system clock by the timer in the controller to extract the elapsed time. When tACS is planned, samples from the various latency distributions are automatically incorporated into the stimulation protocol to match the phase of the projected stimulation targets in time. Using this method, the system avoids the pitfalls of temporal inaccuracies that arise as a result of variable delays intrinsic to any recording/stimulation/processing hardware.

(3.2) Experimental Studies

In experimental studies of the invention, the presence of Slow-wave Oscillations (SWO) was detected, which consist of slow synchronized upward and downward deflections of EEG that are associated with memory consolidation. With tACS, an attempt was made to synchronize and match the stimulation frequency, amplitude, and phase such that maximal stimulation was applied to the UP States (local maxima) of the SWO signal. Prior work suggests that these are the periods during which memories are replayed and consolidated from the hippocampus to the cortex. First, a Virtual Channel (element 306 in FIG. 3) is utilized. An average of EEG signals across multiple recording channels is used to determine the overall synchronous activity of EEG recorded from a human subject during sleep. The Virtual Channel 306 allowed the observation of relatively large SWO oscillation events, while averaging out activity of lesser magnitudes and activity on individual channels unrelated to the pattern of SWO. This Virtual Channel 306 data was stored in a 5-second buffer, on which the prediction algorithm was executed every data collection interval (~2 milliseconds (ms)). The buffer is updated with each discrete data fetch operation that gets new latest data till the point of data request. By the time the buffer is updated, there is a random transmission delay, which needs to be accounted for to plan and precisely time the brain stimulation intervention in the near future.

The frequency of the recorded SWO is obtained by determining the dominant frequency in the power spectrum of the Virtual Channel 306 signal in the buffer. A high-pass filter is applied to center the signal around 0 µV (microvolts). 13 frontal- and centrally-located EEG channels (Cz, FC1, FC2, CP1, CP2, Fz, C4, Pz, C3, F3, F4, P3, P4 (representing different electrode locations) on the international 10-20 layout) are then evaluated to identify outliers, with noisy channels exceeding 250 µV minimum-to-maximum amplitude discarded. The Virtual Channel 306 is constructed by averaging the remaining valid channels. As SWOs occur across regions in the brain, there is the potential for any one electrode channel to become noisy or otherwise unreadable during subject sleep, so utilizing multiple channels to obtain prediction is more robust than relying on any single channel. A Fast Fourier Transformation (FFT) is applied to this virtual channel to identify frequency components of interest (element 310).

SWOs have been observed to have power in the region of 0.5-1.2 Hertz (Hz), and the power within this band is compared to total biologically relevant spectral power of the 5 second interval (i.e., relative spectral power evaluation 312), which includes delta waves (1.5-4.0 Hz), theta waves (4.0-8.0 Hz), spindle activity (8-15 Hz), beta activity (15-25 Hz), and gamma activity (40-120 Hz). Prediction is triggered when the ratio of the SWO power (cumulative sum) to the total power (cumulative sum) exceeds a power threshold, which is personalized to the subject. This personalization is achieved through prior sleep data from the subject obtained through continuous EEG throughout the night. The subject's sleep is staged, the sleep stages S1, S2, S3, and REM are analyzed, and the distribution of 0.5-1.2 Hz band power is taken over each of the stages. SWO activity has been shown to occur during the S3 period, so the relative power threshold is set to the median amplitude of 0.5-1.2 Hz power during S3 sleep per subject.

If the relative power at 0.5-1.2 Hz exceeds the adaptive relative power threshold, the existing frequency transform is then utilized to obtain a frequency-power spectrogram to identify the dominant frequency for the Virtual Channel signal in the buffer (i.e., filter spectral band of interest 314). The precise power peak in the spectrogram is computed to determine the center frequency at which the SWO is most likely to occur. A predictive waveform can then be generated using this center frequency. The phase, offset, and amplitude of the endogenous signal is then computed (element 316) using any of the optimization techniques that are known to those skilled in the art (e.g., linear and nonlinear least-squares regression).

As a preprocessing step, the raw buffer Virtual Channel signal is filtered in the SWO band. FIG. 5 is a plot illustrating an example of filtering raw virtual signal (bold solid line 500) through SWO bandpass window (0.5-1.2 Hz). This filtered signal (unbolded solid line 502) represents the main contribution of the SWO oscillatory activity to the total EEG signal. A sine wave (dashed line 504) is generated by the algorithm and this function can be projected into the future to predict the time points of the UP states in the future (see FIG. 6). By matching the phase of the tACS stimulation to this projected function, the peaks of tACS and the predicted endogenous signal will be aligned.

The ongoing endogenous signal is highly variable and drifts in the frequency, amplitude, and phase domains over time. As a result, predictions derived from data collected further in the past is inherently less reliable due to the potential for rapidly changing signal properties. For this reason, only the most recent data located in the last 80-95% of the filtered buffer signal are used for the predictive waveform, as indicated by the vertical lines (element 506) in FIG. 5.

The analytic signal from this subset of data is obtained by applying a Hilbert transform to the filtered signal, shifting the phase back by 90 degrees, and taking the imaginary component of the complex time series. The Hilbert transform yields complex numbers, which have a real component and an imaginary component. The imaginary component yields the instantaneous phase of the endogenous signal, while its amplitude matches the amplitude of the filtered endogenous signal. With center frequency, phase, offset, and amplitude, a sine wave can now be generated, which serves as an analog for the SWO signal occurring in the future. A mean squared error (MSE) between the generated sine wave and filtered signal data is computed to determine the goodness of fit of the predictive signal (element 318 in FIG. 3). If the MSE is less than a goodness-of-fit threshold, the sine wave is then projected into the future to determine the points of zero phase (i.e., the estimated start of the next UP state), at which time the stimulation intervention is scheduled. In this way, closed-loop brain stimulation can be adapted and applied transiently to match with predicted transient brain states of interest.

Figure 6:
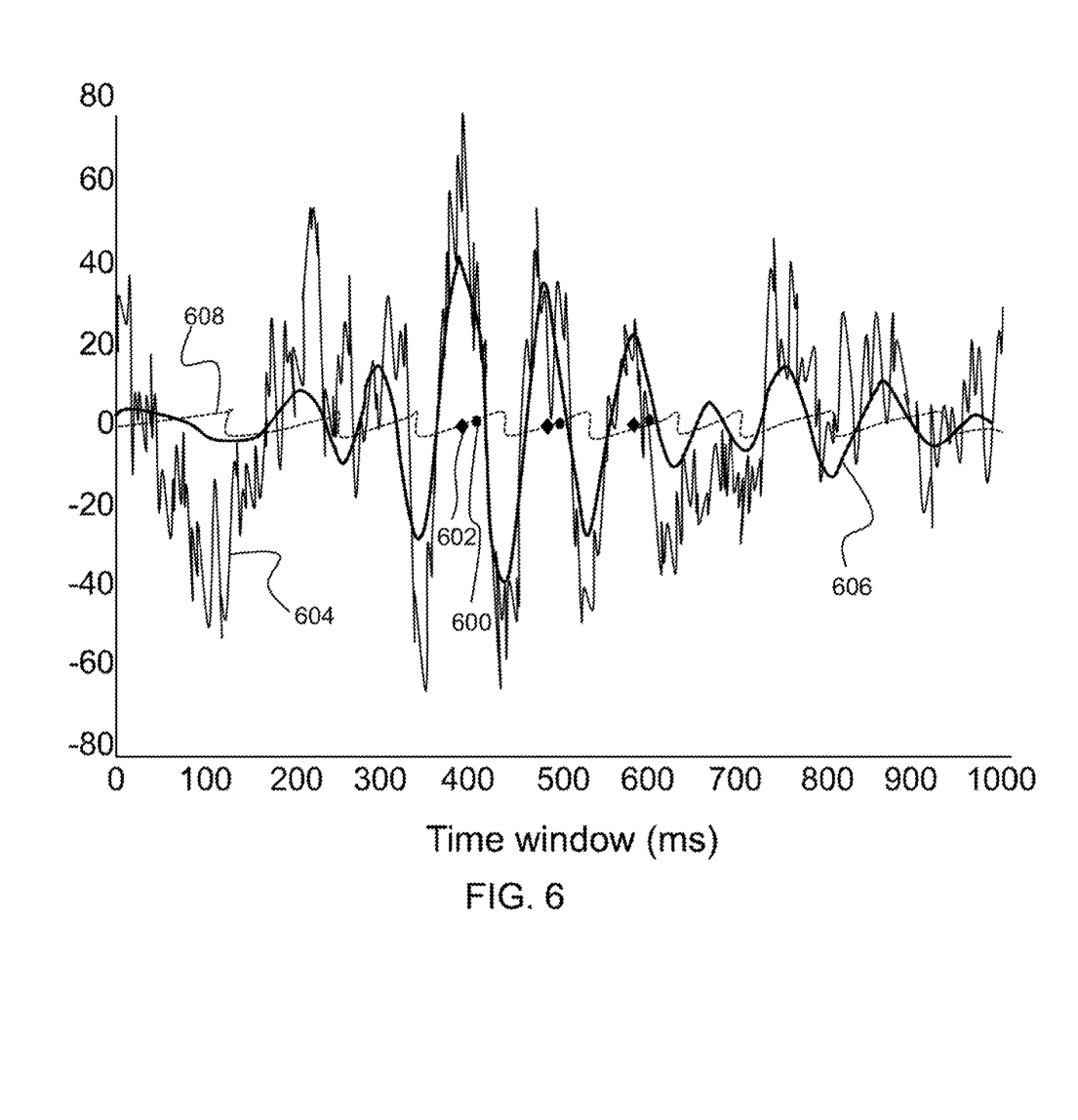
FIG. 6 is an illustration of slow-wave prediction applied to human EEG data according to some embodiments of the present disclosure.

FIG. 6 depicts an example of slow-wave prediction applied to real human EEG data. Predicted peaks of the underlying SWO are denoted as circles 600, while the post-hoc, mathematically computed sine wave representation of the SWO (solid unbolded line 604) defines the putative peaks of SWO denotes as diamonds 602 (i.e., actual location of peaks identified through post-hoc analysis). Solid unbolded line 604 represents the raw EEG, while the solid bold line 606 represents the filtered slow wave oscillation signal. The smaller amplitude represented by the dashed line 608 shows the analytic signal containing phase information.

Figure 7:
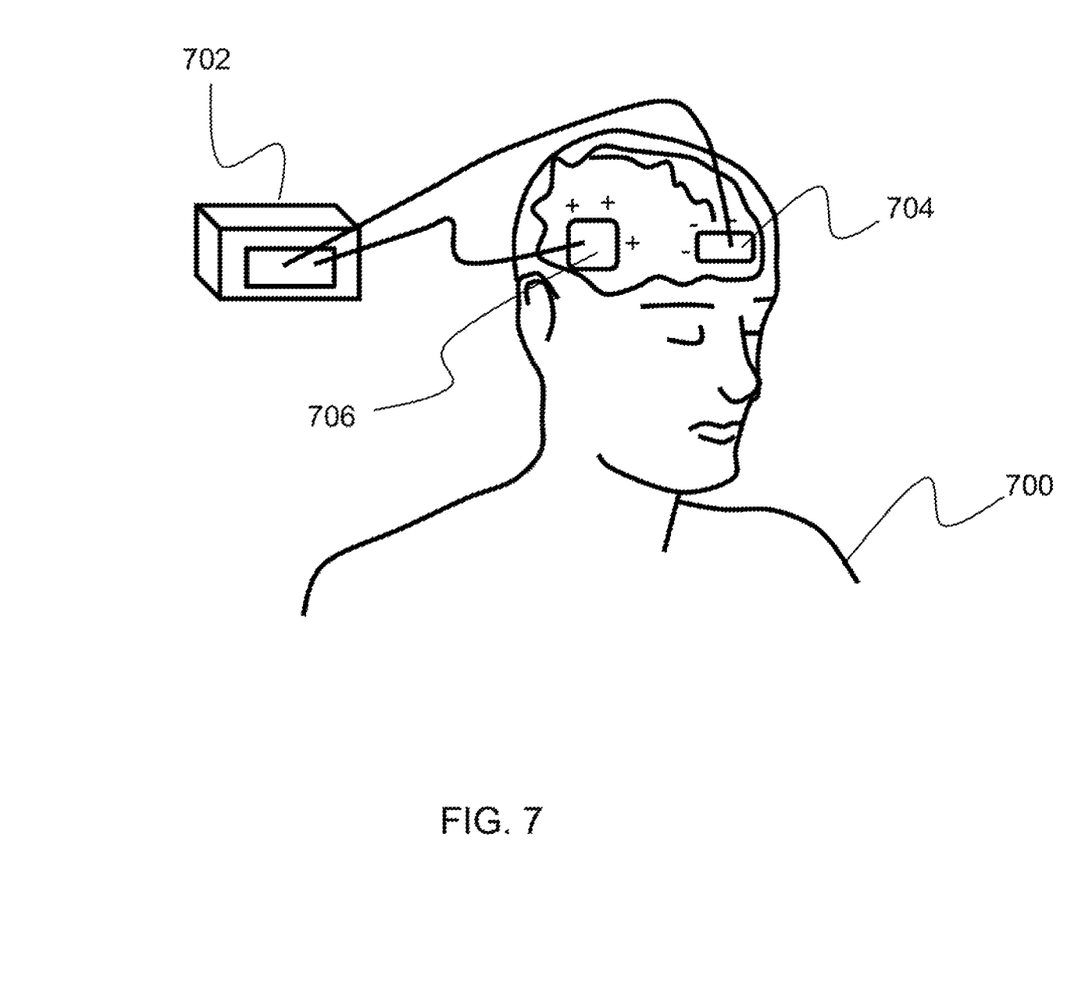
FIG. 7 is an illustration of a human subject receiving neurostimulation via a neural device according to some embodiments of the present disclosure.

FIG. 7 illustrates a human subject 700 receiving a neurostimulation intervention according to some embodiments of the present disclosure. A neural device 702 able to generate an electrical current administers neurostimulation by applying a current through one electrode 704 (e.g., anode), and it flows through the brain to another electrode 706 (e.g., cathode). The neural device 702 is depicted as a patch that adheres to a portion of the patient's head. However, as can be appreciated by one skilled in the art, any suitable neural device 702 can be used (such as a neural cap) provided that it can control stimulation of specific neural regions while performing recordings from the neural device 702 using a targeted arrangement of stimulating electrodes and recording electrodes of the neural device 702.

Because of the number and complexity of computations required for this task, the time elapsed is internally logged during the prediction step of the algorithm using low-level commands to the system clock. The program then determines, based on speed of computation, the precise moment the stimulation should be sent and plans the intervention event appropriately through communication with the brain stimulation hardware. Should computational time exceed the next SWO UP state event (zero phase), the algorithm automatically alters the phase of the stimulation wave in hardware such that the closest alignment with endogenous SWO is achieved.

Current human neurostimulation devices and methods apply stimulation under manual control. This requires a group of expert operators, often in a laboratory environment, to apply interventions to the subject of stimulation (see Literature Reference Nos. 1 and 2). Another limitation of the current state-of-the-art is the non-targeted nature of interventions. Because neurophysiological signals are frequently not monitored in real time, neurostimulative interventions are often made without direct connection to signals of interest. For example, previous studies using tDCS as a skill-training platform (see Literature Reference No. 3) applied this neuromodulatory intervention in general fashion throughout the learning period, rather than during specific activity or in response to particular modes of failure.

The available literature in the field of neurostimulation-based therapy or performance augmentation show markedly different results when the timing and duration of stimulation are changed, which supports the notion that the temporal component of neurostimulation and the particular stimulation protocol used significantly affects efficacy of the intervention (see Literature Reference No. 5). As a result, the technology according to embodiments of the present disclosure substantially improves the ease-of-use, cost, and specificity of nascent neurostimulative devices, which lowers the barrier to entry for a wide range of neurotherapeutic and neuroaugmentative products in development.

Previous research in pilot training and other training programs (see Literature Reference No. 3) relied on manual stimulation of trainee pilot subjects without any specificity in time, which reduced the capabilities of the study and reduced the potential for the commercialization of this technology. Many similar efforts in the field of neurostimulation have similar shortcomings, and the possible use case scenarios for neurostimulation are limited when using non-specifically applied interventions. Further, the current landscape of neurostimulation either forgoes individualized and adaptive stimulation to reduce complexity of devices (Thync, San Francisco; Halo Neuroscience, San Francisco), or achieves fine-grained individualized control of stimulation parameters through the supervision of expert operators or laboratories (see Literature Reference No. 1). These infrastructures are unlikely to be available to end users outside of a research setting.

Additionally, the state-of-the-art currently focuses on the triggering of intervention or predictive detection of brain states in isolation. Leveraging these ideas and implementation to data-driven adaptation and personalization is and has not been obvious due to the fact that the aforementioned components of operation are still in the developmental phase, and also because they have to be instantiated in a real-time system that has various non-zero communication and processing latencies. Because salient, prototypical implementations of these technologies were not extant in the history of the prior art, the capabilities and properties of the technology has (and, to an extent, is), in flux, which has made the conceptualization of complete, synergistic systems exploiting the advantages of the constituent components non-trivial. Further, the utility of the invention is enhanced by the state of the neurotechnology-based appliance market. Contemporary research into various implementations of neurostimulative/neuromodulatory devices and the rise of consumer-level neural stimulation devices drives the need for an effective, sophisticated, and unsupervised control system.

As a result, the closed-loop brain stimulation system according to embodiments of the present disclosure substantially can improve the efficacy of a variety of products. These include:

Therapeutic Deep Brain Stimulators (Parkinson's, Epilepsy, Alzheimer's): Applies non-temporally targeted stimulation, only in laboratory environments (see Literature Reference Nos. 6-8 and 20).

Therapeutic Transcranial Stimulators (Traumatic Brain Injury, Alzheimer's, others): Although devices are portable enough to be used in the field, there is no viable way to apply stimulation without the presence of human operators and so use cases and commercialization opportunities are severely limited (see Literature Reference Nos. 9 and 10).

Skill Training/Performance Augmentation using tCS (memory training, learning aids): Current devices do not record physiological or neural states in real time, and apply a one-size-fits-all stimulation (see Literature Reference Nos. 3 and 11). It is likely the lack of personalization and adaptation to ongoing physiological changes that impact the efficacy of such devices (see Literature Reference No. 5).

Experiential Augmentation (galvanic stimulation): Systems for enhancing or supplementing virtual environment experiences and simulators through neurostimulation have been proposed, particularly for replicating sensations of acceleration and inertia through galvanic vestibular stimulation (GVS) (see Literature Reference No. 12). Such systems would require extensive synergistic interactions between control and stimulation infrastructures to achieve latency-free, realistic effects.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for synchronization of neurostimulation interventions, the system comprising:
   one or more processors and a non-transitory computer-readable medium having executable instructions encoded thereon such that when executed, the one or more processors perform operations of:
   continuously monitoring incoming neurophysiological signals;
   measuring latencies present in the monitoring of the incoming neurophysiological signals;
   based on the measured latencies, determining timing of targeted neurostimulation interventions, resulting in a neurostimulation intervention protocol;
   adjusting the neurostimulation intervention protocol in real time for administration of neurostimulation during temporal regions of interest;
   replicating properties of the incoming neurophysiological signals at the time of neurostimulation; and
   administering the neurostimulation during the temporal regions of interest.

2. The system as set forth in claim 1, wherein the one or more processors further perform operations of classifying the incoming neurophysiological signals and adapting the administered neurostimulation according to the classified incoming neurophysiological signals.

3. The system as set forth in claim 1, wherein the one or more processors further perform an operation of verifying that the administered neurostimulation replicates the properties of the incoming neurophysiological signals.

4. The system as set forth in claim 1, wherein the one or more processors further perform an operation of calibrating the triggering of the administration of the neurostimulation to a set of predetermined neurophysiological signals.

5. The system as set forth in claim 1, wherein the one or more processors further perform an operation of determining potential time points of neurostimulation during which the administered neurostimulation matches predicted neurophysiological signals for slow-wave sleep augmentation.

6. A computer implemented method for synchronization of neurostimulation interventions, the method comprising an act of:
causing one or more processors to execute instructions encoded on a non-transitory computer-readable medium, such that upon execution, the one or more processors perform operations of:
continuously monitoring incoming neurophysiological signals;
measuring latencies present in the monitoring of the incoming neurophysiological signals;
based on the measured latencies, determining timing of targeted neurostimulation interventions, resulting in a neurostimulation intervention protocol;
adjusting the neurostimulation intervention protocol in real time for administration of neurostimulation during temporal regions of interest;
replicating properties of the incoming neurophysiological signals at the time of neurostimulation; and
administering the neurostimulation during the temporal regions of interest.

7. The method as set forth in claim 6, wherein the one or more processors further perform an operation of classifying the incoming neurophysiological signals and adapting the administered neurostimulation according to the classified incoming neurophysiological signals.

8. The method as set forth in claim 6, wherein the one or more processors further perform an operation of verifying that the administered neurostimulation replicates the properties of the incoming neurophysiological signals.

9. The method as set forth in claim 6, wherein the one or more processors further perform an operation of calibrating the triggering of the administration of the neurostimulation to a set of predetermined neurophysiological signals.

10. The method as set forth in claim 6, wherein the one or more processors further perform an operation of determining potential time points of neurostimulation during which the administered neurostimulation matches predicted neurophysiological signals for slow-wave sleep augmentation.

11. A computer program product for synchronization of neurostimulation interventions, the computer program product comprising:
computer-readable instructions stored on a non-transitory computer-readable medium that are executable by a computer having one or more processors for causing the processor to perform operations of:
continuously monitoring incoming neurophysiological signals;
measuring latencies present in the monitoring of the incoming neurophysiological signals;
based on the measured latencies, determining timing of targeted neurostimulation interventions, resulting in a neurostimulation intervention protocol;
adjusting the neurostimulation intervention protocol in real time for administration of neurostimulation during temporal regions of interest;
replicating properties of the incoming neurophysiological signals at the time of neurostimulation; and
administering the neurostimulation during the temporal regions of interest.

12. The computer program product as set forth in claim 11, further comprising instructions for causing the one or more processors to further perform an operation of classifying the incoming neurophysiological signals and adapting the administered neurostimulation according to the classified incoming neurophysiological signals.

13. The computer program product as set forth in claim 11, further comprising instructions for causing the one or more processors to further perform an operation of verifying that the administered neurostimulation replicates the properties of the incoming neurophysiological signals.

14. The computer program product as set forth in claim 11, further comprising instructions for causing the one or more processors to further perform an operation of calibrating the triggering of the administration of the neurostimulation to a set of predetermined neurophysiological signals.

15. The computer program product as set forth in claim 11, further comprising instructions for causing the one or more processors to further perform an operation of determining potential time points of neurostimulation during which the administered neurostimulation matches predicted neurophysiological signals for slow-wave sleep augmentation.

* * * * *